United States Patent [19]

Friederichs

[11] Patent Number: 5,300,616
[45] Date of Patent: Apr. 5, 1994

[54] PROCESS FOR ISOLATING POLYISOCYANATE ISOMERS FROM POLYISOCYANATE MIXTURES

[75] Inventor: Wolfgang Friederichs, Cologne, Fed. Rep. of Germany

[73] Assignee: Bayer Aktiengesellschaft, Leverkusen, Fed. Rep. of Germany

[21] Appl. No.: 998,306

[22] Filed: Dec. 30, 1992

[30] Foreign Application Priority Data

Jan. 8, 1992 [DE] Fed. Rep. of Germany ....... 4200236

[51] Int. Cl.$^5$ .............................. C08G 18/70
[52] U.S. Cl. .................. 528/67; 252/182.21; 252/182.22; 560/336; 560/352
[58] Field of Search ............ 528/67; 252/182.21, 252/182.22; 560/336, 352

[56] References Cited

U.S. PATENT DOCUMENTS

| | | | |
|---|---|---|---|
| 4,246,187 | 1/1981 | Yabroff | 260/453 SP |
| 4,414,074 | 11/1983 | Ellendt et al. | 203/21 |
| 4,499,023 | 2/1985 | Mitrowsky et al. | 260/453 SP |
| 5,043,471 | 8/1991 | Hammen et al. | 560/345 |

FOREIGN PATENT DOCUMENTS

| | | |
|---|---|---|
| 493981 | 4/1972 | Japan . |
| 53-046944 | 4/1978 | Japan . |
| 1417087 | 12/1975 | United Kingdom . |

OTHER PUBLICATIONS

Chemical Abstracts, vol. 89, No. 13, Sep. 25, 1978, Abstract No. 108362w.
Chemical Abstracts, vol. 70, No. 1, Jan. 6, 1969, Abstract No. 3390h.
A. S. Shevlyakov et al., Sin. Fiz.-Khim. Polim., 5, 66 (1968).
CA 70, 3390h 1992.

*Primary Examiner*—Maurice J. Welsh
*Attorney, Agent, or Firm*—Joseph C. Gil; Lyndanne M. Whalen

[57] ABSTRACT

Polyisocyanate mixtures are isolated in pure or more concentrated form from isomeric mixtures by liquid-liquid extraction using a two-phase system. The two phases are 1) a non-polar solvent phase and 2) a polar solution in which a hydrogen halide is present. In a preferred embodiment, the extraction is carried out in a countercurrent extractor.

15 Claims, No Drawings

PROCESS FOR ISOLATING POLYISOCYANATE ISOMERS FROM POLYISOCYANATE MIXTURES

BACKGROUND OF THE INVENTION

The present invention relates to a new process for isolating polyisocyanate mixtures in pure or concentrated form from polyisocyanate mixtures containing at least two polyisocyanate isomers.

It is known that polyisocyanate mixtures can be purified by fractional distillation. For example, in DE-OS 3,145,010, the isolation of high-purity 4,4'-diisocyanato-diphenylmethane (hereinafter referred to as "4,4'-MDI") from a polyisocyanate mixture such as is obtained by phosgenation of aniline/formaldehyde condensation products is disclosed. Disadvantages of this five-stage distillation process are the expense of the apparatus for the multiple distillation of the polyisocyanate mixture and, associated therewith, the high thermal stress of the process product, 4,4'-MDI.

The separation of 2,4'-diisocyanato-diphenylmethane (hereinafter "2,4'-MDI") and 4,4'-MDI from polyisocyanate mixtures of the type described in DE-OS 3,145,010 by distillation and subsequent crystallization is disclosed in DE-OS 2,425,658. In this disclosed process, a distillate containing 2,4'-MDI and 4,4'-MDI is first obtained from the crude polyisocyanate mixture. Cooling of this distillate to a temperature of from 40° C. to 18° C. for 5-6 hours results in the crystallization of high purity 4,4'-MDI. This process is disadvantageous because of the long cooling-down time required for the crystallization and, associated therewith, the strict temperature control requirements.

The continuous separation of polyisocyanate isomer mixtures of tolylene 2,4-diisocyanate (hereinafter "2,4-TDI") and tolylene 2,6-diisocyanate (hereinafter "2,6-TDI") by partial crystallization in a tubular crystallizer is described in DE-OS 3,220,439. In this disclosed process, the isomer mixture is cooled from 30° C. to 6° C. in 5 hours by passing it through a cooled tube. A 2,4-TDI-rich product is obtained after the crystallizate is melted at 20° C. and the mother liquor is drained off. The mother liquor can be further purified. A disadvantage of this process is the long time necessary for the crystallization.

U.S. Pat. No. 4,246,187 discloses a process which is based on the same principle as that disclosed in DE-OS 3,220,439. In the process disclosed in U.S. Pat. No. 4,246,187, the isomer mixture of 2,4-TDI and 2,6-TDI is cooled to a temperature near 6° C. in a heat exchanger in the form of a skimmer centrifuge. The mother liquor obtained is centrifuged off and the crystallizate is continuously discharged. A disadvantage of this process is the technically demanding continuous discharge of solids from the reaction mixture.

In the process described in published Application JP 49 003 981, the stereoisomers of 4,4'-diisocyanato-dicyclohexylmethane (hereinafter "$H_{12}$-MDI"), that is cis,-cis-, cis,trans- and trans,trans-isomers, are separated from aliphatic hydrocarbons by fractional crystallization. To this end, the stereoisomer mixture is dissolved completely at temperatures near 40° C. in the solvent used, and the trans,trans-rich $H_{12}$-MDI isomer mixture crystallizing out on cooling to 10° C. is isolated.

A better separating effect is achieved by the process disclosed in published Application JP 53 046 944. In this disclosed process, the pure trans,trans stereoisomers of the $H_{12}$-MDI are isolated by treating the starting isomer mixture in organic solvents, for example o-chlorobenzene, with gaseous hydrogen chloride. The carbamic acid chlorides which are formed are less soluble than the free isocyanates and precipitate out from the reaction mixture. This process is disadvantageous because of the technical resources required for continuous separation from the reaction mixture of the carbamic acid chloride solids.

The separation of isomer mixtures of 2,4-TDI and 2,6-TDI by introduction of gaseous hydrogen halide into a benzene solution is described by A. S. Shevlyakov et al. in Sin. Fiz.-Khim. Polim., 5, 66 (1968); CA 70, 3390 h.

The known processes either yield the purified polyisocyanate isomers as solids which can not be continuously worked up without the expenditure of large technical resources, or recover the purified polyisocyanate isomers by distillation, which due to the thermal stress associated therewith may result in contamination with by-products.

SUMMARY OF THE INVENTION

It is an object of the present invention to provide a process that permits the isolation under mild conditions of polyisocyanate isomer mixtures from less pure mixtures, less concentrated mixtures or mixtures having different isomer ratios.

It is also an object of the present invention to provide a process for isolating polyisocyanate isomer mixtures in more pure or concentrated form in which solid by-products are not produced.

It is another object of the present invention to provide a process for isolating polyisocyanate isomer mixtures in more pure or concentrated form which may be carried out on an industrial production scale under relatively mild conditions.

These and other objects which will be apparent to those skilled in the art are accomplished by mixing a non-polar organic phase in which a polyisocyanate isomer mixture may optionally be present and a polar solution of an anhydrous hydrogen halide in which a polyisocyanate isomer mixture may optionally be present in a manner such that these phases are intermixed to form a homogeneous mixture. At least one of the non-polar phase and the polar solution must contain a polyisocyanate isomer mixture to be isolated. The homogeneous mixture is then allowed to settle so that two distinct phases form. These phases are then separated and the polyisocyanate isomer mixture present in one or both of these phases is recovered in accordance with techniques known in the art.

DETAILED DESCRIPTION OF THE PRESENT INVENTION

The present invention relates to a process for isolating polyisocyanate isomer mixtures in pure or concentrated form, optionally in the form of their carbamic acid halides, as solutions in aprotic organic solvents from polyisocyanate mixtures containing at least two different isomers. In this process, a two-phase system made up of a) a non-polar organic solvent phase, that optionally contains isomeric polyisocyanates to be recovered in pure or concentrated form in the polar solution, and b) a polar solution of an anhydrous hydrogen halide, that is present in a less than stoichiometric amount (relative to the total amount of polyisocyanates present) that optionally contains isomeric polyisocyanates to be recovered in pure or concentrated form in the non-polar solvent
is first homogenized by intermixing the phases. The phases which subsequently separate are then isolated. Each of these phases may then be further extracted. That is, the non-polar solvent phase may optionally be extracted again with a polar solvent phase of the same type as b) described above and/or the polar solvent phase may be extracted again with a non-polar solvent phase of the same type as a). The phase in which the polyisocyanate isomers are present in pure or concentrated form may then be worked up using techniques known in the art.

The intermixing and subsequent separation of the phases is preferably carried out in a single-stage or multistage countercurrent extractor.

The non-polar solvent phase obtained during the first extraction is preferably subjected to a countercurrent multistage extraction with a polar phase of the same type as b) which was described above.

The polar solvent phase obtained during the first extraction may also preferably be subjected to a countercurrent multistage extraction with a non-polar phase of the same type as a) which was described above.

Preferably at least one of the solvent phases obtained is worked up by distillation. It is also preferred that the polyisocyanate mixture obtained be freed from hydrogen halides by heat treatment at temperatures of from 20° C. to 200° C.

The polyisocyanates partition themselves in a two-phase system between the two phases. In the application to multicomponent systems (polyisocyanate mixture), a concentration of one or several isomers of the isomeric polyisocyanate mixture in one of the two phases is achieved. This concentration also occurs if the extraction of the polyisocyanates is carried out in the absence of hydrogen halides. The concentration of one or several polyisocyanate isomers in one of the two phases is, however, more effective if hydrogen halides are included in the multicomponent system. As a result of the reactivity differences between the various isocyanate groups in polyisocyanate isomers, the isomers with the more reactive groups concentrate in the polar phase.

The starting materials for the process according to the invention are crude polyisocyanate mixtures such as those which are obtained during large-scale production (e.g., by phosgenation of the polyamines on which they are based). Preferred starting materials include polyisocyanate mixtures containing at least two stereoisomeric and/or position-isomeric polyisocyanates. Especially preferred polyisocyanate mixtures are the isomer mixtures of the polyisocyanates commonly used in the production of polyurethanes such as tolylene diisocyanate, diisocyanato-diphenylmethane (optionally in presence of other oligomeric derivatives), 1,4′-diisocyanato-cyclohexane and 4,4′-diisocyanato-dicyclohexylmethane.

All polar solvents which: 1) are liquid under the process conditions; 2) dissolve the products of the process under the process conditions; 3) are inert with respect to isocyanates, carbamic acid halides and hydrogen halides under the process conditions; and 4) have at least one miscibility gap with the non-polar solvent under the process conditions are suitable for the polar solutions used in the process of the present invention. Specific examples of suitable polar solvents (i.e., solvents satisfying the above-enumerated criteria) include: aliphatic sulfones such as diethyl sulfone, dipropyl sulfone, dibutyl sulfone and ethyl propyl sulfone; cyclic sulfones such as sulfolane, 2-methylsulfolane, 3-methylsulfolane, 2,4-dimethylsulfolane; aromatic nitrocompounds such as nitrobenzene, 2-nitrotoluene, 3-nitrotoluene, 4-chloronitrobenzene; aliphatic nitriles such as acetonitrile; and mixtures of such compounds. Acetonitrile, sulfolane and 3-methylsulfolane are preferred polar solvents.

Any non-polar solvent which: 1) is liquid under the process conditions; 2) dissolves the products of the process under the process conditions; 3) is inert with respect to isocyanates, carbamic acid halides and hydrogen halides under the reaction conditions; and 4) has at least one miscibility gap with the polar solvent under the process conditions is suitable as a non-polar solvent in the process of the present invention. Specific examples of suitable non-polar solvents satisfying these criteria include: aliphatic hydrocarbons such as n-hexane, i-octane, and gasoline fractions; cycloaliphatic hydrocarbons such as cyclohexane and methylcyclohexane; aromatic hydrocarbons such as benzene and toluene; and mixtures of such compounds. n-Hexane, i-octane, cyclohexane and methylcyclohexane are preferred non-polar solvents.

The polyisocyanate mixtures to be treated in accordance with the present invention may be added to the polar, hydrogen-halide-containing solvent phase, or to the non-polar solvent phase or to both. The concentration of the polyisocyanates corresponds to their solubility and to the solubility of the corresponding carbamic acid halides in the solvents used. Usually, 1–50 wt % solutions are used. Preferably, at least 5 wt % solutions are used because at smaller concentrations poor space-time yields are attained.

Hydrogen chloride, hydrogen bromide or mixtures of these hydrogen halides are generally used as the hydrogen halide. Obviously, compounds which will release hydrogen halide under the process conditions may also be used. Suitable hydrogen-halide-releasing compounds include: ammonium halides derived from tertiary amines which are soluble in polar solvents such as trimethylammonium chloride, triethylammonium bromide, and methyldiphenylammonium chloride; primary carbamic acid halides such as N-methylcarbamic acid chloride and N-phenylcarbamic acid chloride; and preferably the carbamic acid halides derived from the polyisocyanates to be separated.

The volume ratios between polar and non-polar phase in all stages of the process according to the invention can vary between wide limits. The optimum ratio will depend upon the specific mixture to be separated. Ratios which have been found to be advantageous are 1:10 to 10:1, preferably 1:5 to 5:1.

In all stages of the process of the present invention, the amount of halogen halide added is preferably chosen so that in the polar phase up to 1 mole hydrogen halide is present for each mole of the polyisocyanates to be separated in the polar phase.

The manner in which the hydrogen halide is introduced to the system is of secondary importance in the process of the present invention. The hydrogen halide may, for example, be dissolved in one of the two phases or in both phases. It is also possible to convert a part of the polyisocyanate mixture to be separated to the corresponding carbamic acid halides by reaction with gaseous hydrogen halide prior to extraction and then to feed the hydrogen halide to the system in combined form, preferably in the polar solvent phase.

The design of the extraction apparatus used to carry out the process of the present invention is of secondary importance. Devices customary for analogous chemical separating operations may be used. Examples of suitable apparatus include multistage countercurrent extraction columns and mixer-settler batteries connected in series. The process of the present invention is preferably carried out using 5- to 15-stage countercurrent extraction columns.

The process is carried out in all stages under temperature and pressure conditions such that both phases are liquid. It is preferred that the process be carried out within the temperature range from 10° C. to 150° C. at normal pressure. It may be appropriate to carry out individual stages of the process at different temperatures. The application of excess or reduced pressure may be appropriate in some cases.

The non-polar phase is preferably worked up by removing the solvent by distillation. The resulting mixture of polyisocyanate isomers, that optionally contains small amounts of carbamic acid halides, can be freed from residual amounts of hydrogen halide by heat-treating at temperatures sufficient to at least partly dissociate the carbamic acid chloride to free isocyanate and hydrogen halide, optionally while passing an inert gas stream through the reaction vessel. In general, the heat-treatment step is carried out at temperatures of from 20° to 200° C.

Obviously the polyisocyanate isomer mixture may also be processed further without a preliminary heat treatment. Such heat treatment is unnecessary, for example, when the mixture is to be used for a process in which the presence of hydrogen halides does not interfere or is possibly even desirable.

The polar phase, which in general contains a large part of the hydrogen halide used in the form of carbamic acid halides, may be worked up in the same way as the non-polar phase.

The non-polar and/or polar phase may be returned to the extraction process in whole or in part. In many cases, it may be advantageous to use the carbamic acid halide present in the polar phase as hydrogen-halide-releasing compound for the process according to the invention. To this end, the polar phase may be used without further purification. The polar phase may also be concentrated by distilling off the solvent or a part of the solvent before reusing it in the process of the present invention.

The non-polar and/or polar phase can obviously be extracted again by repeating the above-described process steps in order to obtain a more effective isolation of the polyisocyanate isomers in pure or concentrated form.

The following examples provide a more detailed explanation of the process of the present invention without restricting it. All parts and percentages given in these Examples are parts by weight and percentages by weight, unless otherwise indicated.

EXAMPLES

Example 1

In a 10-stage mixer-settler system at 40° C., a solution of 385 g of a tolylene diisocyanate mixture (isomer mixture of 35 wt % 2,6-isomer and 65 wt % 2,4-isomer) and 80 g hydrogen chloride in 440 g anhydrous acetonitrile and a solution of 165 g of a tolylene diisocyanate mixture (isomer mixture of 35 wt % 2,6-isomer and 65 wt % 2,4-isomer) in 1450 g anhydrous cyclohexane were run in countercurrent to each other.

1000 ml/h of the acetonitrile solution and 2000 g/h of the cyclohexane solution were passed through. After a period of about 4 h, an equilibrium had been achieved. 1770 g/h acetonitrile phase and 715 g/h cyclohexane phase were obtained as process products. According to gas chromatography, the acetonitrile phase contained 285 g/kg tolylene diisocyanate mixture (an isomer mixture of 33 wt % 2,6-isomer and 67 wt % 2,4-isomer). Some of the tolylene diisocyanates were present in the form of the corresponding carbamic acid chlorides. The cyclohexane phase contained 67 g/kg tolylene diisocyanate mixture (isomer mixture of 59 wt % 2,6-isomer and 41 wt % 2,4-isomer).

Therefore, from the tolylene diisocyanate isomer mixture used (isomer ratio 35:65), two new isomer mixtures with the isomer ratios 33:67 and 59:41 were recovered.

Example 2

A solution of 265 g hydrogen chloride in 2250 g sulfolane freshly made absolute was added to a solution of 2000 g of a diisocyanato-diphenylmethane mixture (isomer mixture of 50 wt % 4,4'-isomer and 50 wt % 2,4'-isomer) in 8000 g anhydrous cyclohexane. After 1 h of vigorous stirring at 40° C. the phases were separated. 4450 g sulfolane phase and 8350 g cyclohexane phase were obtained. According to gas chromatography, the sulfolane phase contained 1645 g diisocyanato-diphenylmethane mixture (isomer mixture of 56 wt % 4,4'-isomer and 44 wt % 2,4'-isomer), in which a part of the diisocyanato-diphenylmethane was present in the form of the corresponding carbamic acid halides. After removal of the solvent in a rotary evaporator, the cyclohexane phase provided 355 g diisocyanato-diphenylmethane mixture (isomer mixture of 23 wt % 4,4'-isomer and 77 wt % 2,4'-isomer).

Therefore, from the diisocyanato-diphenylmethane isomer mixture used (isomer ratio 50:50), two new isomer mixtures with isomer ratios 56:44 and 23:77 were recovered.

Example 3

To a solution of 3.0 kg of a 4,4'-diisocyanato-dicyclohexylmethane mixture (isomer mixture of 27 wt % cis,cis-isomer, 50 wt % cis,trans-isomer and 23 wt % trans,trans-isomer) in 9.0 kg anhydrous cyclohexane was added a solution of 300 g hydrogen chloride in 5.4 kg anhydrous acetonitrile. After 1 h of vigorous stirring at 30° C. the phases were separated. 9.8 kg acetonitrile phase and 7.9 kg cyclohexane phase were obtained. After the solvent was removed, the cyclohexane phase yielded 800 g 4,4'-diisocyanato-dicyclohexylmethane mixture (isomer mixture of 36 wt % cis,cis-isomer, 50 wt % cis,trans-isomer and 14 wt % trans,trans-isomer).

To this mixture there were added 2.4 kg anhydrous cyclohexane and a solution of 85 g hydrogen chloride in 1.4 kg anhydrous acetonitrile. After 1 h of vigorous stirring at 30° C., the phases were separated. 2.9 kg acetonitrile phase and 1.8 kg cyclohexane phase were obtained. After removal of the solvent, the cyclohexane phase yielded 135 g 4,4'-diisocyanato-dicyclohexylmethane mixture (isomer mixture of 44 wt % cis,cis-isomer, 46 wt % cis,trans-isomer and 10 wt % trans,trans-isomer).

From the isomer mixture used (isomer ratio 27:50:23), a new isomer mixture with an isomer ratio of 44:46:10 was recovered.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for isolating mixtures of polyisocyanate isomers or carbamic acid halides of polyisocyanate isomers in more pure or concentrated form from a mixture of at least two different polyisocyanate isomers or carbamic acid halides of polyisocyanate isomers in an aprotic organic solvent comprising
    a) mixing a two-phase system composed of
        1) a non-polar solvent and
        2) a polar solution of an anhydrous halide in which the isomer mixture to be isolated in more pure or concentrated form is present in at least one of 1) and 2) until the system is homogeneous,
    b) allowing the distinct phases to form, and
    c) separating the phases formed in b).

2. The process of claim 1 in which a polyisocyanate isomer mixture to be isolated is present in both non-polar solvent a) and polar solution b).

3. The process of claim 1 in which it least one of the phases separated in c) is subjected to further extraction.

4. The process of claim 1 in which the non-polar solvent phase separated in c) is further extracted with a polar solvent.

5. The process of claim 1 in which the polar solvent phase separated in c) is further extracted with a non-polar solvent.

6. The process of claim 1 in which at least one of the polyisocyanates in the mixture to be isolated is present in the form of its corresponding carbamic acid halide.

7. The process of claim 1 in which a countercurrent extractor is employed.

8. The process of claim 1 in which a multistage countercurrent extractor is employed.

9. The process of claim 1 in which the non-polar solvent phase separated in c) is further extracted with a polar solvent by multistage countercurrent extraction.

10. The process of claim 1 in which the polar solvent phase separated in c) is further extracted with a non-polar solvent by multistage countercurrent extraction.

11. The process of claim 1 in which the polyisocyanate mixture includes at least two stereoisomers or position isomers.

12. The process of claim 1 in which the polyisocyanate mixture is a mixture selected from isomeric mixtures of tolylene diisocyanate, isomeric mixtures of diisocyanato-diphenylmethane, isomeric mixtures of diisocyanato-cyclohexane, and isomeric mixtures of diisocyanato-dicyclohexylmethane.

13. The process of claim 1 in which at least one of the phases separated in c) is distilled.

14. The process of claim 13 in which the polyisocyanates obtained as products of the distillation are freed from any hydrogen halide by heat treatment.

15. The process of claim 14 in which the heat treatment is carried out at a temperature of from about 20 to about 200° C.

* * * * *